US010340101B2

(12) United States Patent
Varghese et al.

(10) Patent No.: US 10,340,101 B2
(45) Date of Patent: Jul. 2, 2019

(54) KEYCAP WITH ACTIVE ELEMENTS

(71) Applicant: Intel Corporation, Santa Clara, CA (US)

(72) Inventors: Reji Varghese, Bangalore (IN); Ayeshwarya B. Mahajan, Bangalore (IN); Peter Bonesio, Mesa, AZ (US); Ramesh Pendakur, Bangalore (IN); Sukanya Sundaresan, Karnataka (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/749,393

(22) PCT Filed: Apr. 2, 2016

(86) PCT No.: PCT/US2016/025767
§ 371 (c)(1),
(2) Date: Jan. 31, 2018

(87) PCT Pub. No.: WO2017/023371
PCT Pub. Date: Feb. 9, 2017

(65) Prior Publication Data
US 2018/0226210 A1    Aug. 9, 2018

(30) Foreign Application Priority Data

Jul. 31, 2015  (IN) .......................... 3958/CHE/2015
Jul. 31, 2015  (IN) .......................... 3959/CHE/2015
Jul. 31, 2015  (IN) .......................... 3961/CHE/2015

(51) Int. Cl.
*H01H 13/83*    (2006.01)
*H01H 13/79*    (2006.01)
(Continued)

(52) U.S. Cl.
CPC .......... *H01H 13/83* (2013.01); *A61B 5/0402* (2013.01); *A61B 5/0537* (2013.01);
(Continued)

(58) Field of Classification Search
CPC ..................................................... H01H 13/83
(Continued)

(56) References Cited

U.S. PATENT DOCUMENTS 4,551,717 A    11/1985  Dreher
4,853,888 A     8/1989  Lata et al.
(Continued)

FOREIGN PATENT DOCUMENTS

CN     1575486 A     2/2005
CN     1620707 A     5/2005
(Continued)

OTHER PUBLICATIONS

International Search Report and Written Opinion in International Patent Application No. PCT/US2016/025767 dated Jul. 20, 2016, 9 pages).
(Continued)

*Primary Examiner* — Qutbuddin Ghulamali
(74) *Attorney, Agent, or Firm* — Patent Capital Group

(57) ABSTRACT

Particular embodiments described herein provide for a keycap. The keycap can include a protective layer and an active element, where the height of protective layer and the active element is less than six (6) millimeters in height. The keycap can also include a front plane layer, a back plane layer, where the front plane layer and the back plane layer comprise the active element, and an electrical connection through the keycap to provide electrical communication with the active element.

20 Claims, 10 Drawing Sheets

(51) Int. Cl.
*A61B 5/0402* (2006.01)
*A61B 5/053* (2006.01)
*A61B 5/00* (2006.01)
*G06F 3/023* (2006.01)
*H01H 13/705* (2006.01)
*H01H 3/12* (2006.01)
*H01H 13/704* (2006.01)
*H01H 13/7065* (2006.01)

(52) U.S. Cl.
CPC .......... *A61B 5/6897* (2013.01); *A61B 5/6898* (2013.01); *G06F 3/0233* (2013.01); *G06F 3/0238* (2013.01); *H01H 13/705* (2013.01); *H01H 13/79* (2013.01); *H01H 3/125* (2013.01); *H01H 13/704* (2013.01); *H01H 13/7065* (2013.01); *H01H 2203/038* (2013.01); *H01H 2219/002* (2013.01); *H01H 2219/01* (2013.01); *H01H 2219/012* (2013.01); *H01H 2219/02* (2013.01); *H01H 2227/026* (2013.01)

(58) Field of Classification Search
USPC .......................................................... 341/23
See application file for complete search history.

(56) References Cited

U.S. PATENT DOCUMENTS

| | | | |
|---|---|---|---|
| 6,704,004 | B1 | 3/2004 | Östergård et al. |
| 6,797,902 | B2 | 9/2004 | Farage et al. |
| 6,798,359 | B1 | 9/2004 | Ivancic |
| 6,898,299 | B1 | 5/2005 | Brooks |
| 8,350,728 | B2 * | 1/2013 | Liu .................. H03M 11/06 341/22 |
| 2002/0022113 | A1 | 2/2002 | Kimura |
| 2003/0058223 | A1 | 3/2003 | Tracy et al. |
| 2004/0217939 | A1 | 11/2004 | Levy et al. |
| 2006/0179088 | A1 * | 8/2006 | Kang .................. G06F 3/0238 708/142 |
| 2007/0021677 | A1 | 1/2007 | Markel |
| 2008/0011596 | A1 | 1/2008 | Lee et al. |
| 2008/0024425 | A1 | 1/2008 | Shido |
| 2008/0179173 | A1 | 7/2008 | Jung et al. |
| 2011/0056814 | A1 | 3/2011 | Cheng |
| 2011/0148766 | A1 | 6/2011 | Huang |
| 2013/0076634 | A1 | 3/2013 | Pedersen et al. |
| 2014/0028564 | A1 | 1/2014 | Valentine et al. |
| 2015/0084871 | A1 | 3/2015 | Yarvis et al. |
| 2015/0157220 | A1 | 6/2015 | Fish et al. |
| 2016/0157781 | A1 | 6/2016 | Baxi et al. |
| 2018/0158625 | A1 | 6/2018 | Mahajan et al. |
| 2018/0199887 | A1 | 7/2018 | Mahajan et al. |
| 2018/0233307 | A1 | 8/2018 | Sundaresan et al. |

FOREIGN PATENT DOCUMENTS

| | | |
|---|---|---|
| CN | 1815425 A | 8/2006 |
| CN | 201846526 U | 5/2011 |
| JP | 2004184945 A | 7/2004 |
| JP | 2008250259 A | 10/2008 |
| KR | 20110068209 A | 6/2011 |
| WO | 2017023371 A1 | 2/2017 |
| WO | 2017023372 A1 | 2/2017 |

OTHER PUBLICATIONS

International Search Report and Written Opinion in International Patent Application No. PCT/US2016/025768 dated Jul. 12, 2016, 9 pages).
USPTO Non-Final Office Action issued in U.S. Appl. No. 15/716,554 dated Jul. 11, 2018 (10 pages).
USPTO Non-Final Office Action issued in U.S. Appl. No. 15/749,483 dated Jul. 25, 2018 (24 pages).
USPTO Final Office Action issued in U.S. Appl. No. 15/749,483 dated Feb. 21, 2019; 15 pages.
USPTO Non-Final Office Action issued in U.S. Appl. No. 15/744,373 dated Mar. 11, 2019 (47 pages).

* cited by examiner

KEYCAP WITH ACTIVE ELEMENTS

CROSS-REFERENCE TO RELATED APPLICATIONS

This Application is a national stage application under 35 U.S.C. § 371 of PCT Application PCT/US2016/025767, filed Apr. 2, 2016 and entitled "KEYCAP WITH ACTIVE ELEMENTS", which claims priority to Provisional Application No. 3958/CHE/2015, entitled "BI-STABLE DISPLAY" filed in the Indian Patent Office on Jul. 31, 2015, to Provisional Application No. 3961/CHE/2015, entitled "KEYBOARD WITH DISPLAY EMBEDDED KEYS AND DEVICE TO SENSE BIO-SIGNALS" filed in the Indian Patent Office on Jul. 31, 2015, and to Provisional Application No. 3959/CHE/2015, entitled "KEYCAP WITH ACTIVE ELEMENTS" filed in the Indian Patent Office on Jul. 31, 2015, which are hereby incorporated by reference in their entirety.

TECHNICAL FIELD

This disclosure relates in general to the field of electronic devices, and more particularly, to a keycap with active elements.

BRIEF DESCRIPTION OF THE DRAWINGS

To provide a more complete understanding of the present disclosure and features and advantages thereof, reference is made to the following description, taken in conjunction with the accompanying FIGURES, embodiments are illustrated by way of example and not by way of limitation in the FIGURES of the accompanying drawings, in which like references indicate similar elements and in which.

DETAILED DESCRIPTION OF EXAMPLE EMBODIMENTS

Example Embodiments

Figure 1A:
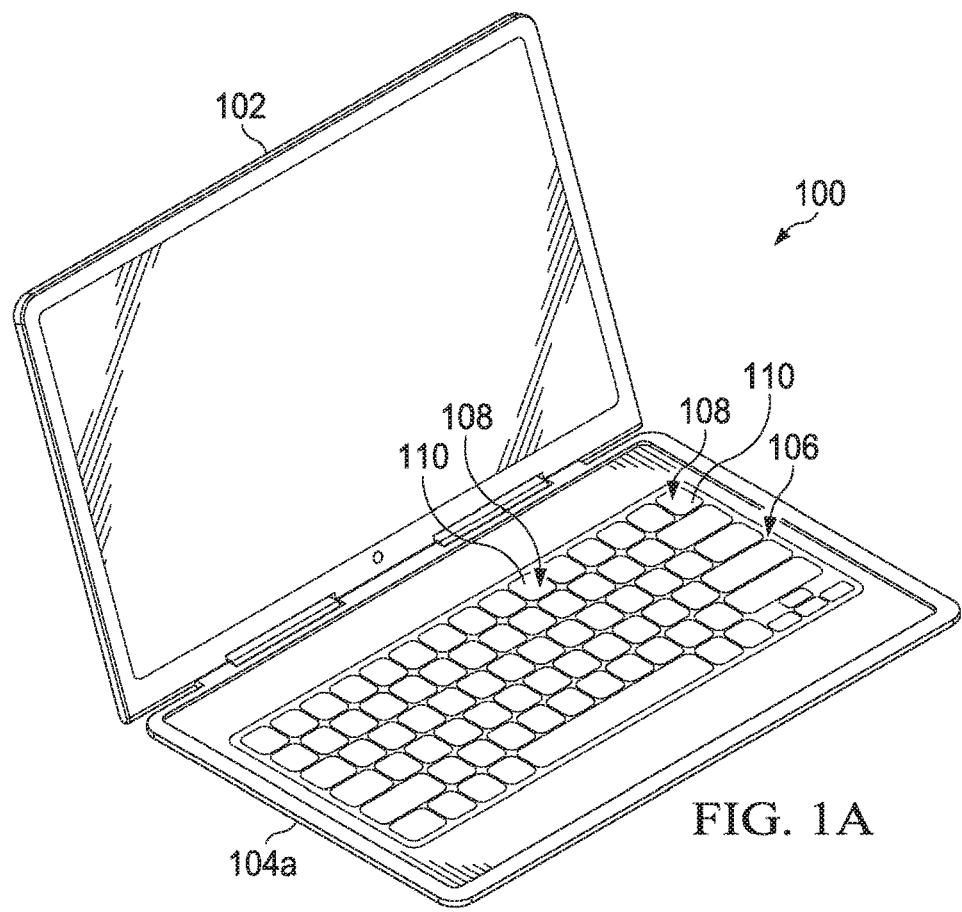
FIG. 1A is a simplified schematic diagram illustrating a perspective view of an embodiment of an electronic device, in accordance with one embodiment of the present disclosure.

FIG. 1A is a simplified schematic diagram illustrating an embodiment of an electronic device 100 in accordance with one embodiment of the present disclosure. Electronic device 100 can include a first housing 102 and a second housing 104a. Second housing 104a can include a physical keyboard portion 106. Keyboard portion 106 can include keys 110 and each key can include a keycap 108. In one or more embodiments, electronic device 100 may be any suitable electronic device having a keyboard or keys such as a laptop, a notebook that includes keys, a desktop computer, a mobile device that includes keys, a tablet device that includes keys, a Phablet™ that includes keys, a personal digital assistant (PDA) that includes keys, an audio system that includes keys, a movie player of any type that includes keys, remote control that includes keys, etc.

Figure 1B:
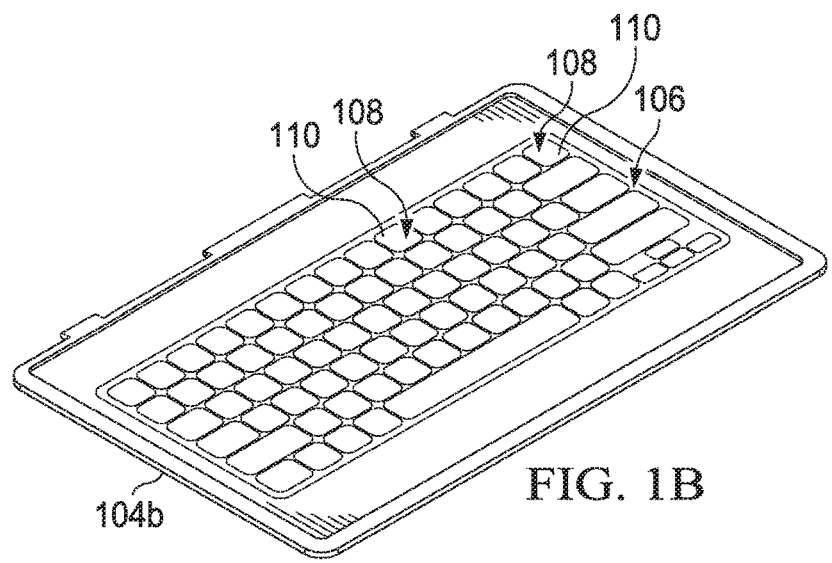
FIG. 1B is a simplified schematic diagram illustrating a perspective view of an embodiment of an electronic device, in accordance with one embodiment of the present disclosure.

Turning to FIG. 1B, FIG. 1B is a simplified schematic diagram of a detachable second housing 104b in accordance with one embodiment of the present disclosure. Detachable second housing 104b can include keyboard portion 106 and keys 110 where each key includes keycap 108. Second housing 104b may also be a standalone keyboard in communication with an electronic device (e.g., a Bluetooth™ keyboard in wireless communication with a computing device like smartphone, desktop, or laptop, a keyboard connected to a computing device through a wire or cable like USB or PS2). In some examples, keyboard portion 106 may be physically attached to an electronic device (e.g. a keyboard integrated into the chassis of an electronic device such as a laptop or electronic device 100).

For purposes of illustrating certain example features of a keycap (e.g., keycap 108) with an active element, the following foundational information may be viewed as a basis from which the present disclosure may be properly explained. A keycap of a keyboard is a small mechanical component that travels up and down when the key is pressed by a user. A typical keycap includes a curved surface on the top to provide ergonomic comfort when a finger of a user rests on the keycap. The typical keycap also includes a fine textured surface to prevent a glossy/shining finish and to provide a subtle grip for a finger of a user when the finger presses the key. Some keycaps include a label (either printed or etched) on a topmost surface of keycap to provide a wide angle of view (almost 180 degree) and allow identification of the key. In addition, a typical keycap can include a locking mechanism on the bottom side to provide mechanical (usually a snap fit) connection with rest of the keyboard subsystem. The thickness of the keycap is typically relatively small. For example, a typical thickness at a periphery and at the locking mechanism is usually around about two (2) millimeters (mm) while the thickness in other areas is often around one (1) mm. Most keycaps are designed to withstand multi-million operations.

One problem with keycaps is that the keycap is typically a passive mechanical component and has a static appearance and function. The keycap does not contain any active element like a display or sensor. One reason for this is because given the thin mechanical profile, surface topology and texture, viewing angle, and lifetime requirements, it is difficult to embed an active element inside the keycap without compromising on one or more of the features of the typical keycap.

An electronic device whose keys include keycaps with embedded active elements, as outlined in FIGS. 1A and 1B, can resolve these issues (and others). For example, keycap 108 can be configured to include an embedded active element such as a display. In a specific implementation, an optically clear and free flowing (very low viscosity) resin may be used as part of the construction of the keycap with the embedded active element.

More specifically, the keycap design can include a pocket where an active subsystem (e.g., a display and its electrical interface) can be housed. The pocket with the active element can be filled with a resin causing the active subsystem to be fully immersed in a very thin layer of resin. The resin can be cured where it transforms into a solid while adhering to the keycap structure, thereby making the active subsystem an integral part of the keycap itself. The resin flow, quantity/thickness, and curing process can be controlled to ensure typical keycap requirements are not compromised in a way that negatively impacts a user experience or that impacts the user experience in a negative manner.

The electrical connection to the active subsystem can be established in a number of ways. For example, by making vias, holes, pass through, etc. in the keycap and filling them with conductive epoxy. These vias can then be connected to an active element using conductive adhesive. Similarly, a PCB may be placed in a slot in the keycap or conductive traces can be created directly on the keycap using processes like LDS, two-shot injection, LCP, or other means may be used. In each case the active element is connected to the conductive traces using Z-axis adhesive.

The dimensions/thickness of keycap 108 are not increased from a typical thickness of a passive keycap. In an example, the dimensions/thickness of keycap are not increased above about 2 millimeters (mm) and the weight is about the same as a passive keycap (e.g., about 0.8 grams). In a specific example, a typical thickness of a passive keycap can be about 1.7 to about 2.2 mms in thickness and the conversion of the passive keycap to an active keycap does not increase the thickness of the keycap. The visual appearance and texture feel of the keycap can be about the same as the passive keycap. If the active element is a display, a graphic displayed on keycap 108 can have a wide angle view similar to a default keycap with a printed or etched label as the graphic is still almost on the surface of the keycap. The electrical connection to couple the active element with a subsystem can be achieved by means that are constructed to be inherently part of an existing keycap without requiring any external electro mechanical components. Resin based encapsulation enables creating a single part that provides a high level of protection to the active element from humidity/water, from external mechanical interactions such as from fingernails and can be scratch resistant while at the same time largely retaining the overall visual appearance and texture feel as a default passive key. In other embodiments, a graphic can be created on the surface of keycap 108 as in conventional keycaps by painting and etching processes with the display segments acting as the backlight for each graphic.

In other embodiments, electrical connection can be established using a PCB instead of conductive vias. For example, a slot can be made in keycap 108 where the PCB is inserted. The PCB can be of suitable materials like FR-4, Polyimide, PET, etc. Other embodiments include creating conductive traces directly on the keycap surface using processes like LDS, two-shot injection, LCP, etc.

In yet another embodiment, a pocket can be created on the bottom side of the key instead of on top of the key, that is, the keycap top surface can form the pocket. In this instance, a locking mechanism may be prepared as a separate unit which is bonded to the top surface of the keycap containing the active element with resin, for example, during assembly such as a bottom load process. These embodiments can be used to embed active elements, such as sensors, displays, etc. within keycap 108 without modifying its fundamental structure and typing experience. This can result in development of many new custom form factors, experiences and capabilities for computing devices like PC, tablet, phone & accessories.

Figure 2:
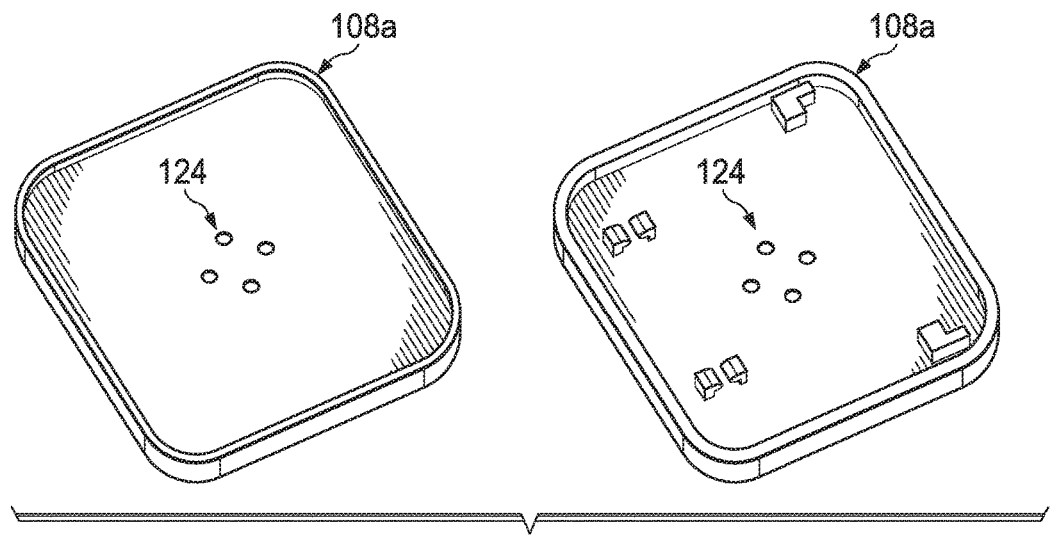
FIG. 2 is a simplified schematic diagram illustrating a perspective view of an embodiment of a portion of a keycap, in accordance with one embodiment of the present disclosure.

Turning to FIG. 2, FIG. 2 is a simplified schematic diagram illustrating an embodiment of a keycap 108a in accordance with one embodiment of the present disclosure. Keycap 108a can include a plurality of vias 124 (e.g., through holes) to allow an electrical connection to pass through keycap 108a. In an embodiment, the dimensions of keycap 108a is not increased from a typical keycap (e.g., about 1.8 to about 2 mm in thickness). In another embodiment, the dimensions/thickness of keycap 108 are not increased above about 6 mm or, in another embodiment, above about 2 mm and the weight is about the same as a passive keycap (e.g., about 0.8 grams or less than about 1 gram).

Figure 3A:
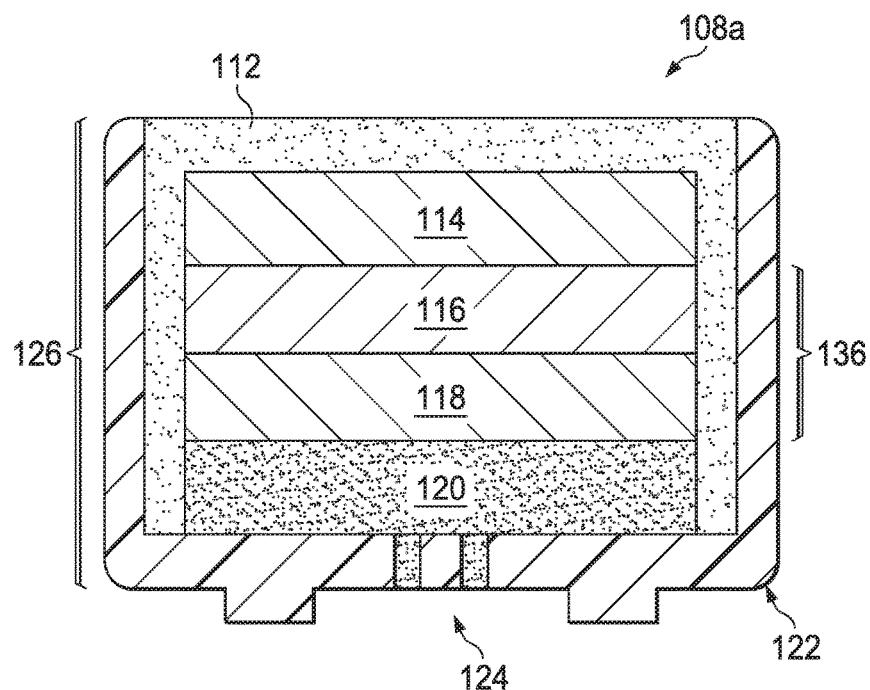
FIG. 3A is a simplified schematic diagram illustrating a side view of an embodiment of a portion of a keycap, in accordance with one embodiment of the present disclosure.

Turning to FIG. 3A, FIG. 3A is a simplified schematic diagram illustrating an embodiment of keycap 108a in accordance with one embodiment of the present disclosure. In an example, keycap 108a can include a resin layer 112, a mask layer 114, a front plane layer 116, a backplane layer 118, and a Z axis conductive adhesive layer 120. Front plane layer 116 and backplane layer 118 can comprise a display 136. Display 136 may be a bi-stable segmented display element. Resin layer 112, mask layer 114, front plane layer 116, backplane layer 118, and adhesive layer 120 can be contained within a pocket 122 of keycap 108a. Pocket 122 may include a plastic wall and plurality of vias 124 may be filled with conductive epoxy. A combined thickness 126 of resin layer 112, mask layer 114, front plane layer 116, backplane layer 118, and adhesive layer 120 can be less than about 6 mm or, in another embodiment, less than about 2 mm. All these elements can be configured to act as a single part that largely retains the visual appearance and texture feel of a passive keycap.

Figure 3B:
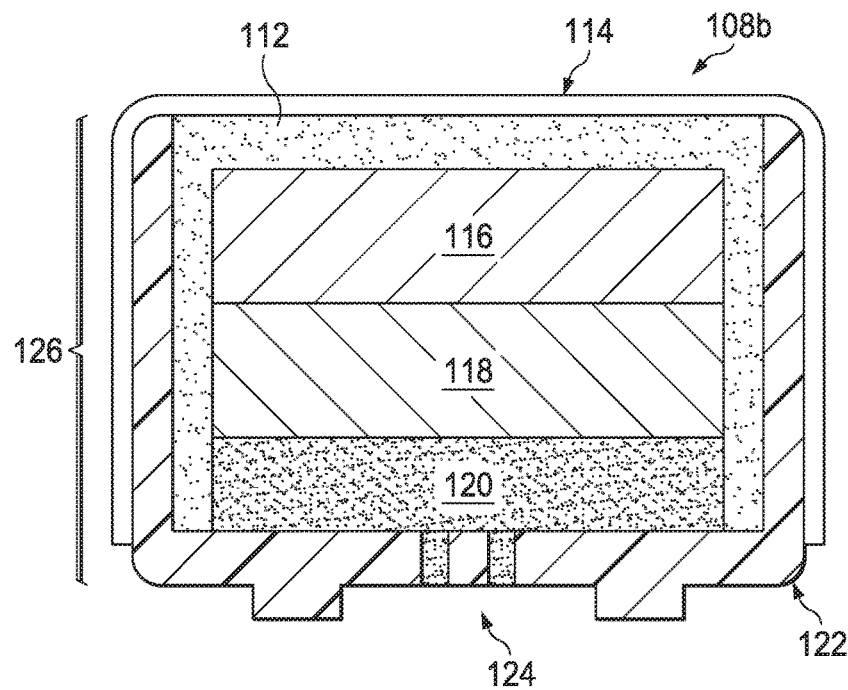
FIG. 3B is a simplified schematic diagram illustrating a side view of an embodiment of a portion of a keycap, in accordance with one embodiment of the present disclosure.

Turning to FIG. 3B, FIG. 3B is a simplified schematic diagram illustrating an embodiment of keycap 108b in accordance with one embodiment of the present disclosure. In an example, keycap 108b can include resin layer 112, mask layer 114, front plane layer 116, backplane layer 118, and Z axis conductive adhesive layer 120. Resin layer 112, front plane layer 116, backplane layer 118, and adhesive layer 120 can be contained within pocket 122 of keycap 108b. Pocket 122 may include a plastic wall and plurality of vias 124 filled with conductive epoxy. In an example, one or more graphics can be created on mask layer 114 on the surface of keycap 108b by a painting and an etching processes with display segments acting as backlight for each graphic on mask layer 114.

In an example, resin layer 112 can be optically clear while providing a concave surface and texture. The curvature and texture of the surface of keycap 108a can be varied depending on design requirements. Mask layer 114 can be about seven (7) microns (e.g., using direct print) to about forty-seven (47) microns thick (e.g., using a sticker with OCA). Front plane layer 116 may be less than about two-hundred and fifty (250) microns thick or about one-hundred and seventy-five (175) microns thick and include ITO, PET, eink, etc. Backplane layer 118 may be less than about two-hundred (200) microns thick or about one-hundred and ten (110) microns thick and include carbon and PET. Backplane layer 118 may form display segments in a segmented display. Z axis adhesive layer 120 may be less than one-hundred (100) microns thick or about fifty (50) microns thick and can include some form of adhesive that serves the dual purpose of adhesion and enabling electrical connectivity between vias 124 and backplane layer 118. The visual appearance and texture feel of a passive keycap is largely retained.

Keycap 108a can be configured to replace a static keycap label with an active element (e.g., bi-stable ePaper display). For example, keycap 108a can be constructed with an embedded active element using an optically clear and free flowing (e.g., low or very low viscosity) resin for constructing the keycap with an embedded active element (e.g., a display). The active element and its electrical interface can be housed in a pocket of keycap 108a.

The dimensions/thickness of keycap 108a is not increased from the typical 1.8 to 2 mm thickness of a passive keycap and the visual appearance and texture feel of the keycap can be the same as a passive keycap. In an example, the dimensions/thickness of keycap are not increased above about 6 mm or, in another embodiment, above about 2 mm and the weight is about the same as a passive keycap (e.g., about 0.8 grams or less than 1 gram). In an example, a graphic displayed on keycap 108a can have a wide angle view like a typical keycap with a printed (or etched) label. In addition, keycap 108a does not require new electro-mechanical components to establish an electrical connection to the active element. Also, because the resin based encapsulation is a single part design, the results can include a higher protection to active element from humidity and water and from external mechanical interactions such as from fingernails and can be scratch resistant. Further, the overall visual appearance and usage feel of a key with keycap 108a can be the same or about the same as typical passive key.

Figure 4:
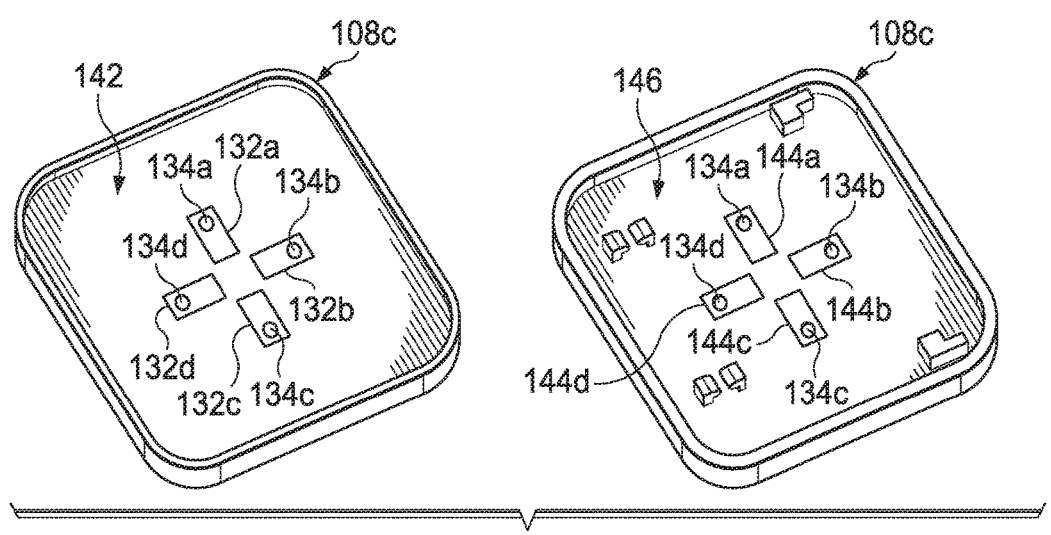
FIG. 4 is a simplified schematic diagram illustrating a perspective view of an embodiment of a portion of a keycap, in accordance with one embodiment of the present disclosure.

Turning to FIG. 4, FIG. 4 is a simplified schematic diagram illustrating an embodiment of a keycap 108c in accordance with one embodiment of the present disclosure. Keycap 108c can include a plurality of pocket connection areas 132a-132d on a pocket side 142 of keycap 108b that are in a pocket of keycap 108b and can provide electrical communication with display 136. Keycap 108b can include a plurality of dome connection areas 144a-144d on a dome side 146 of keycap 108b that can provide electrical communication with a dome or other mechanical feature of a keyboard. Pocket connection areas 132a-132d and dome connection areas 144a-144d can be in electrical communication using vias 134a-134d respectively. Pocket connection areas 132a-132d, vias 134a-134d, and dome connection areas 144a-144d can be created using processes like LDS, LCP, two shot injection, etc. In an example, vias 134a-134d are not filled with epoxy and a conductive path is created only along the internal wall of each via 134a-134d. Active elements can be coupled or connected to pocket connection areas 132a-132d through adhesive layer 120 to allow for a communication path through keycap 108b. In an embodiment, the dimensions of keycap 108b are not increased from a typical keycap (e.g., about 1.7 mms to about 2.2 mms in thickness). In another embodiment, the dimensions/thickness of keycap are not increased above about 6 mm or, in another embodiment, above about 2 mm and the weight is about the same as a passive keycap (e.g., about 0.8 grams or less than 1 gram). In an illustrative example, using an LDS or LCP process to create dome connection areas 144a-144d, the location of vias 134a-134d can be almost anywhere along each dome connection area 144a-144d. For example, they could be at the periphery of keycap 108c. In some instances, vias 134a-134d need to be covered with a water resistant coating/material and may be located outside a dome contact area to allow flexibility to easily apply water resistant coating. If vias 134a-134d are located in a dome contact area, the water resistant coating needs to be applied with very high precision to ensure the conductive contact area with the dome is not reduced.

Figure 5:
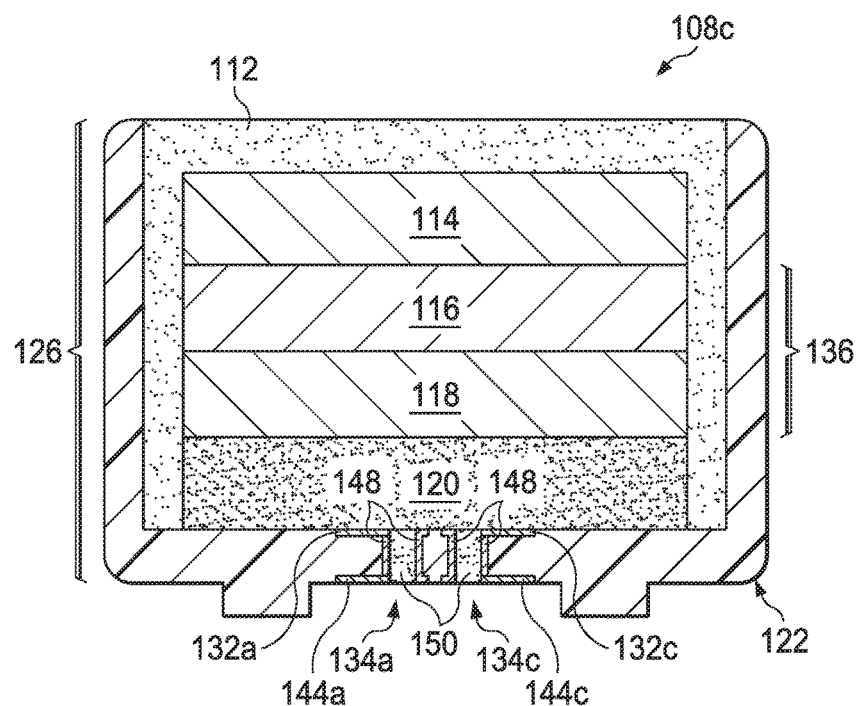
FIG. 5 is a simplified schematic diagram illustrating a side view of an embodiment of a portion of a keycap, in accordance with one embodiment of the present disclosure.

Turning to FIG. 5, FIG. 5 is a simplified schematic diagram illustrating an embodiment of keycap 108c in accordance with one embodiment of the present disclosure. In an example, keycap 108c can include resin layer 112, mask layer 114, front plane layer 116, backplane layer 118, and Z-axis adhesive layer 120. Front plane layer 116 and backplane layer 118 can comprise display 136. Resin layer 112, mask layer 114, front plane layer 116, backplane layer 118, and adhesive layer 120 can be contained within pocket 122 of keycap 108c. Pocket 122 may include a wall and vias 134a-134d created directly on keycap 108c using processes like LDS, LCP, two shot injection, etc. A conductive material 148 may be coupled to the inside walls of vias 134a-134d to allow pocket connection areas 132a-132d to be coupled or in communication with dome connection areas 144a-144d. Vias 134a-134d can be filled with a water resistant material 150 to help mitigate or avoid ingress of water through vias 134a-134d. A thickness 126 of resin layer 112, mask layer 114, front plane layer 116, backplane layer 118, and adhesive layer 120 may be less than about 6 mm or, in another embodiment, above about 2 mm thick. In an example, mask layer 114 may be located outside pocket 122 similar to keycap 108b illustrated in FIG. 3B.

The dimensions/thickness of keycap 108c are not increased from the typical about 1.7 to about 2.2 mm thickness of a passive keycap and the visual appearance and texture feel of the keycap can be the same as a passive keycap. In an example, a graphic displayed on keycap 108b can have a wide angle view like a typical keycap with a printed (or etched) label. In addition, keycap 108b does not require new electro-mechanical components to establish an electrical connection to the active element. Also, because the resin based encapsulation is a single part design, the results can include a higher protection to active element from humidity and water and from external mechanical interactions such as from fingernails and can be scratch resistant. Further, the overall visual appearance and usage feel of a key with keycap 108b can be the same or about the same as typical passive key.

Figure 6:
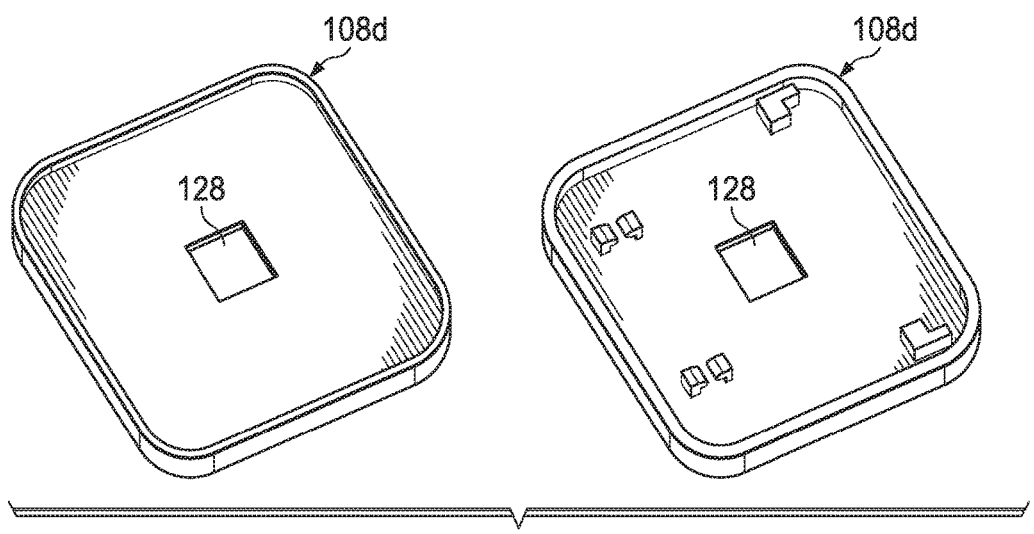
FIG. 6 is a simplified schematic diagram illustrating a perspective view of an embodiment of a portion of a keycap, in accordance with one embodiment of the present disclosure.

Turning to FIG. 6, FIG. 6 is a simplified schematic diagram illustrating an embodiment of a keycap 108d in accordance with one embodiment of the present disclosure. Keycap 108c can include a slot 128 to allow a PCB to be inserted or coupled to keycap 108d. The PCB can be made of any suitable material like FR-4, Polyimide, PET, etc. As in the case of vias, a conductive adhesive can be used between the PCB and an active element such as a display (e.g., display 136). In another embodiment, the active element can also be such that it has a step that fits in the slot of the keycap, thus, not requiring any other interconnect mechanism. In an embodiment, the dimensions of keycap 108c are not increased from a typical keycap (e.g., about 1.8 to about 2 mm in thickness). In another embodiment, the dimensions/thickness of keycap are not increased above about 6 mm or, in another embodiment, above about 2 mm and the weight is about the same as a passive keycap (e.g., about 0.8 grams or less than 1 gram).

Figure 7:
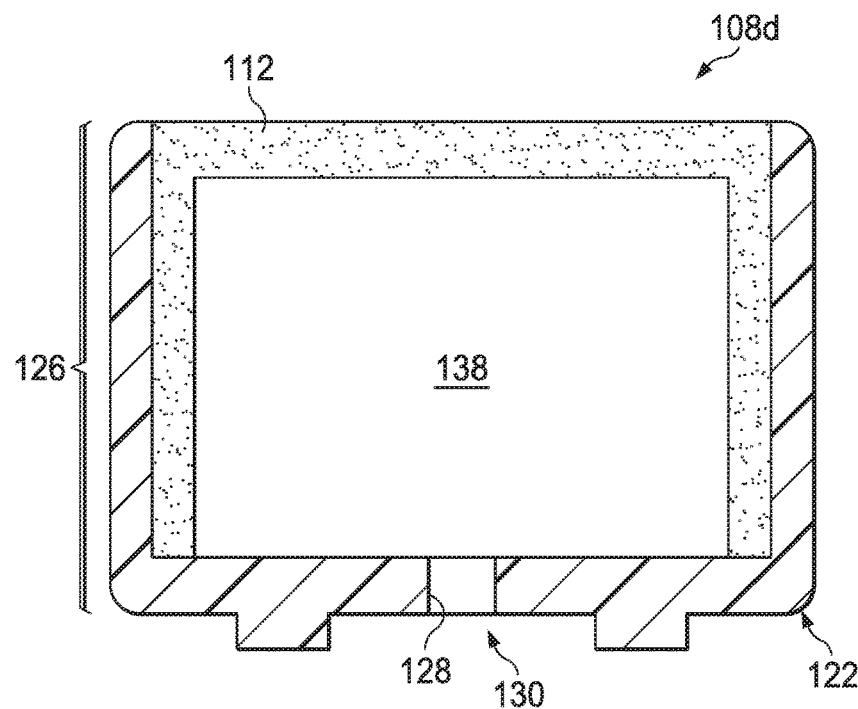
FIG. 7 is a simplified schematic diagram illustrating a side view of an embodiment of a portion of a keycap, in accordance with one embodiment of the present disclosure.

Turning to FIG. 7, FIG. 7 is a simplified schematic diagram illustrating an embodiment of keycap 108c in accordance with one embodiment of the present disclosure. In an example, keycap 108c can include an active element 138. Pocket 122 may include a plastic wall and a PCB 130 can be contained in slot 128 in keycap 108c. A thickness 126 of active element 138 may be less than about 6 mm or, in another embodiment, less than about 2 mm thick. Active element 138 can be configured as an active element and include circuits such as sensors placed on a thin substrate like polyimide. For example, an IR sensor for temperature measurement, PPG sensor for heart rate measurement, etc. In an example, active element 138 may be a display. It should be noted that key caps 108a-108c can also include active element 138 rather than resin layer 112, mask layer 114, front plane layer 116, backplane layer 118, and/or Z-axis adhesive layer 120.

Figure 8:
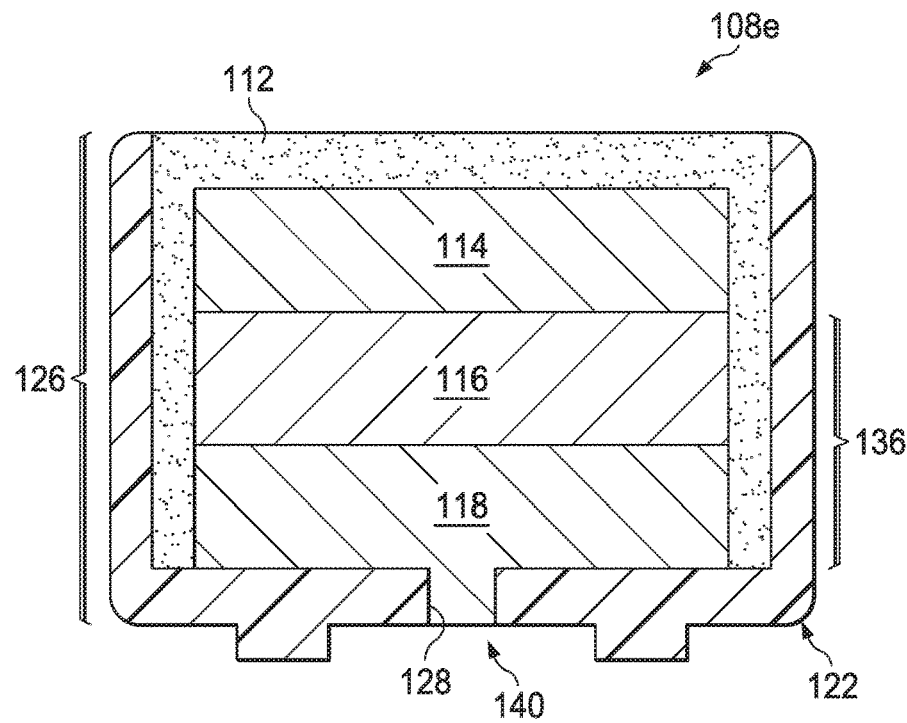
FIG. 8 is a simplified schematic diagram illustrating a side view of an embodiment of a portion of a keycap, in accordance with one embodiment of the present disclosure.

Turning to FIG. 8, FIG. 8 is a simplified schematic diagram illustrating an embodiment of keycap 108d in accordance with one embodiment of the present disclosure. In an example, keycap 108d can include resin layer 112, mask layer 114, front plane layer 116, and backplane layer 118. Front plane layer 116 and backplane layer 118 can comprise display 136. Resin layer 112, mask layer 114, front plane layer 116, and backplane layer 118 can be contained within pocket 122 of keycap 108d. Backplane layer 118 can include an interconnect step 140 that is an extension of its structure such that when display 136 is placed in pocket 122 of keycap 108c, interconnect step 140 can provide an electrical pathway or communication between display 136 and some other electronic element or device in communication with keycap 108c.

The dimensions/thickness of keycap 108c are not increased from the typical 1.7 to 2.2 mms thickness of a passive keycap and the visual appearance and texture feel of the keycap can be the same as a passive keycap. In an example, a graphic displayed on keycap 108c can have a wide angle view like a typical keycap with a printed (or etched) label. In addition, keycap 108c does not require new electro-mechanical components to establish an electrical connection to the active element (e.g., display 136). Also, because the resin based encapsulation is a single part design, the results can include a higher protection to active element from humidity and water and from external mechanical interactions such as from fingernails and can be scratch resistant. Further, the overall visual appearance and usage feel of a key with keycap 108c can be the same or about the same as typical passive key.

Figure 9:
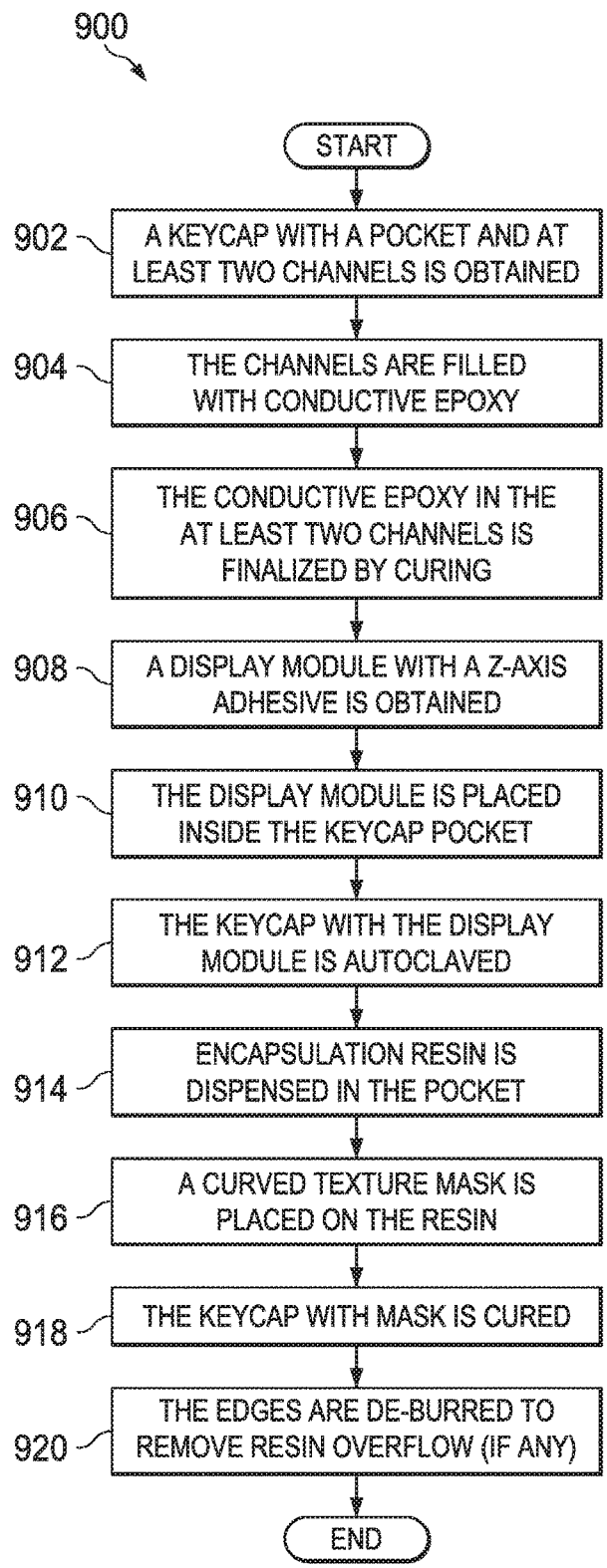
FIG. 9 is a simplified flow diagram illustrating potential operations associated with one embodiment of the present disclosure.

Turning to FIG. 9, FIG. 9 is an example flowchart illustrating possible operations of a flow 900 that may be associated with making a keycap that includes an active element. In this specific example, the active element is a display and may be a bistable segmented display. At 902, a keycap with a pocket and at least two channels (e.g., vias 124) is obtained. Alternatively, the keycap may contain a slot or have conductive traces directly created on the keycap. At 904, the channels are filled with conductive epoxy. In an example, the conductive epoxy can be conductive silver epoxy or an equivalent material. Alternatively, a PCB could be placed into the slot in the keycap and the channels may not be filled with epoxy as the conductive traces can be directly created using LCP. In case of an LDS/LCP process the channels may be fill via with a water resistant material as illustrated in FIG. 5. At 906, the conductive epoxy in the at least two channels is finalized by curing. At 908, a display module with a Z axis adhesive is obtained. In an example, the display module is a bi-stable segmented display. At 910, the display module is placed inside the keycap pocket. At 912, the keycap with the display (and the Z-axis adhesive) is autoclaved. At 914, encapsulation resin is dispensed in the pocket. In an example, low viscosity encapsulation resin is dispended in the pocket using calibrated target dispensing pressure and volume. At 916, a curved texture mask is placed on the resin. At 918, the keycap with the mask is cured. At 920, the edges are de-burred to remove any resin overflow.

Figure 10:
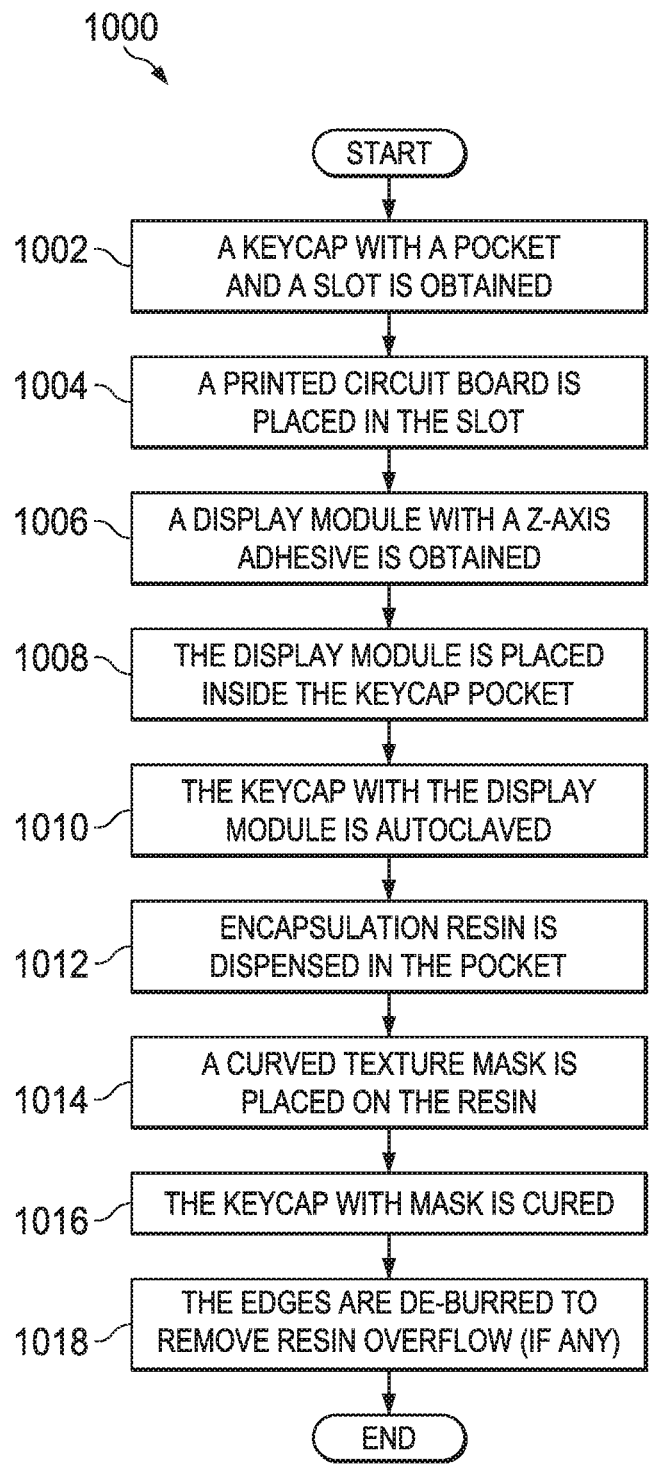
FIG. 10 is a simplified flow diagram illustrating potential operations associated with one embodiment of the present disclosure.

Turning to FIG. 10, FIG. 10 is an example flowchart illustrating possible operations of a flow 1000 that may be associated with making a keycap that includes an active element. In this specific example, the active element is a display and may be a bistable segmented display. At 1002, a keycap with a pocket and a slot is obtained. At 1004, a PCB is placed into the slot. In an example, the PCB can include conductive traces. The PCB can be made of any suitable material such as FR-4, Polyimide, PET, etc. At 1006, a display module with z-axis adhesive is obtained. At 1008, the display module is placed inside the keycap pocket. At 1010, the keycap with the display module (and the Z-axis adhesive) is autoclaved. At 1012, encapsulation resin is dispensed in the pocket. In an example, low viscosity encapsulation resin is dispended in the pocket using calibrated target dispensing pressure and volume. At 1014, a curved texture mask is placed on the resin. At 1016, the keycap with the mask is cured. At 1018, the edges are de-burred to remove any resin overflow.

The operations of flow 900 and 1000 can be used to embed active elements (e.g., sensors, displays, etc.) on or in keycap 108. The process can be used to facilitate many use cases in a keyboard without modifying the keyboards fundamental structure and without drastically altering or negatively affecting the typing experience. The process can also facilitate the development of many new custom form factors, capabilities and experiences for PC, tablet, phone & accessories.

Figure 11:
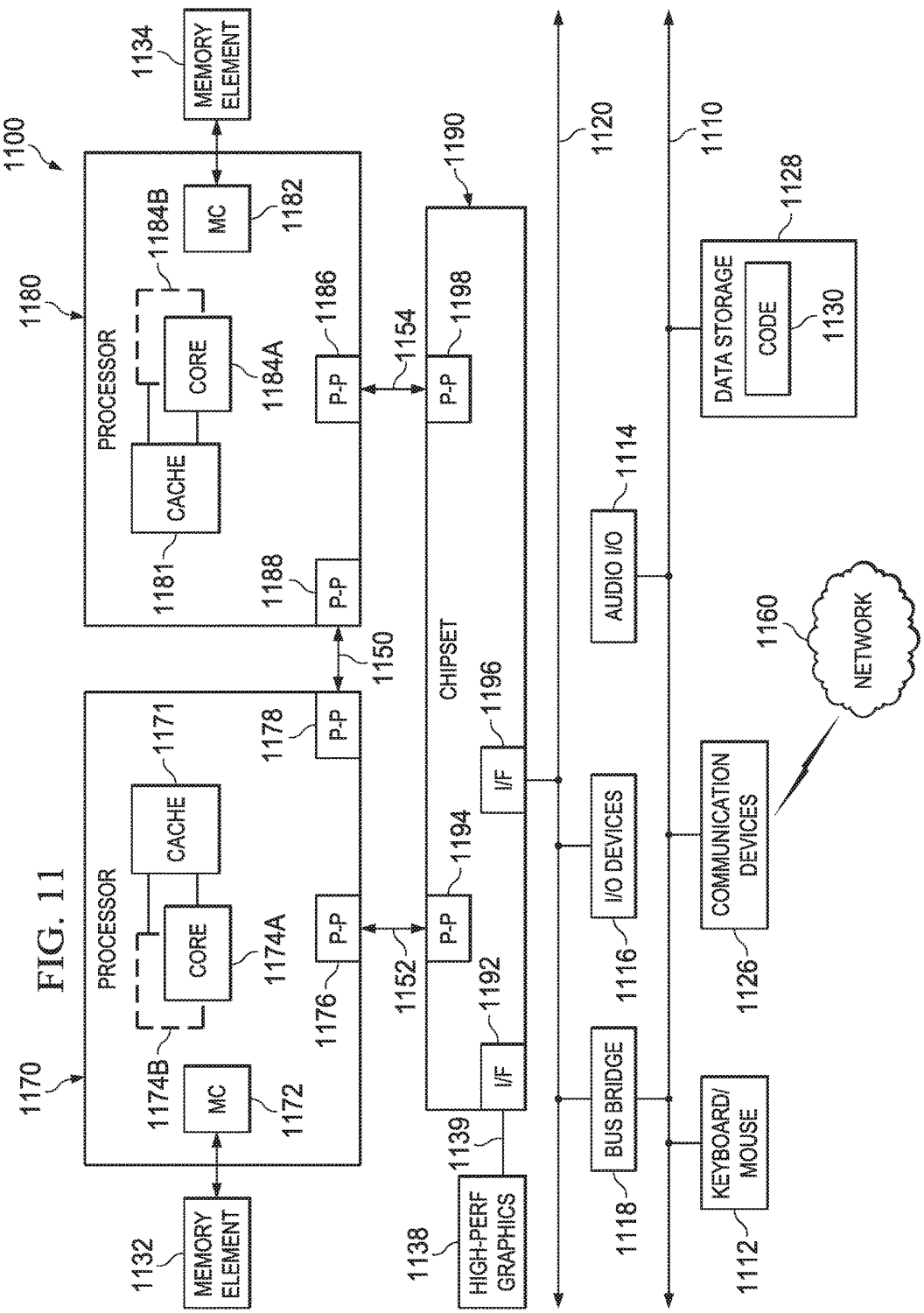
FIG. 11 is a block diagram illustrating an example computing system that is arranged in a point-to-point configuration in accordance with an embodiment.

Turning to FIG. 11, FIG. 11 illustrates a computing system 1100 that is arranged in a point-to-point (PtP) configuration according to an embodiment. In particular, FIG. 11 shows a system where processors, memory, and input/output devices are interconnected by a number of point-to-point interfaces. Generally, one or more of the elements of electronic device 100 may be configured in the same or similar manner as computing system 1100.

As illustrated in FIG. 11, system 1100 may include several processors, of which only two, processors 1170 and 1180, are shown for clarity. While two processors 1170 and 1180 are shown, it is to be understood that an embodiment of system 1100 may also include only one such processor. Processors 1170 and 1180 may each include a set of cores (i.e., processor cores 1174A and 1174B and processor cores 1184A and 1184B) to execute multiple threads of a program. Each processor 1170, 1180 may include at least one shared cache 1171, 1181. Shared caches 1171, 1181 may store data (e.g., instructions) that are utilized by one or more components of processors 1170, 1180, such as processor cores 1174 and 1184.

Processors 1170 and 1180 may also each include integrated memory controller logic (MC) 1172 and 1182 to communicate with memory elements 1132 and 1134. Memory elements 1132 and/or 1134 may store various data used by processors 1170 and 1180. In alternative embodiments, memory controller logic 1172 and 1182 may be discreet logic separate from processors 1170 and 1180.

Processors 1170 and 1180 may be any type of processor and may exchange data via a point-to-point (PtP) interface 1150 using point-to-point interface circuits 1178 and 1188, respectively. Processors 1170 and 1180 may each exchange data with a chipset 1190 via individual point-to-point interfaces 1152 and 1154 using point-to-point interface circuits 1176, 1186, 1194, and 1198. Chipset 1190 may also exchange data with a high-performance graphics circuit 1138 via a high-performance graphics interface 1139, using an interface circuit 1192, which could be a PtP interface circuit. In alternative embodiments, any or all of the PtP links illustrated in FIG. 11 could be implemented as a multi-drop bus rather than a PtP link.

Chipset 1190 may be in communication with a bus 1120 via an interface circuit 1196. Bus 1120 may have one or more devices that communicate over it, such as a bus bridge 1118 and I/O devices 1116. Via a bus 1110, bus bridge 1118 may be in communication with other devices such as a keyboard/mouse 1112 (or other input devices such as a touch screen, trackball, etc.), communication devices 1126 (such as modems, network interface devices, or other types of communication devices that may communicate through a computer network 1160), audio I/O devices 1114, and/or a data storage device 1128. Data storage device 1128 may store code 1130, which may be executed by processors 1170 and/or 1180. In alternative embodiments, any portions of the bus architectures could be implemented with one or more PtP links.

The computer system depicted in FIG. 11 is a schematic illustration of an embodiment of a computing system that may be utilized to implement various embodiments discussed herein. It will be appreciated that various components of the system depicted in FIG. 11 may be combined in a system-on-a-chip (SoC) architecture or in any other suitable configuration. For example, embodiments disclosed herein can be incorporated into systems including stand-alone keyboards and devices that include keyboards or keys. It will be appreciated that these devices may be provided with SoC architectures in at least some embodiments.

Figure 12:
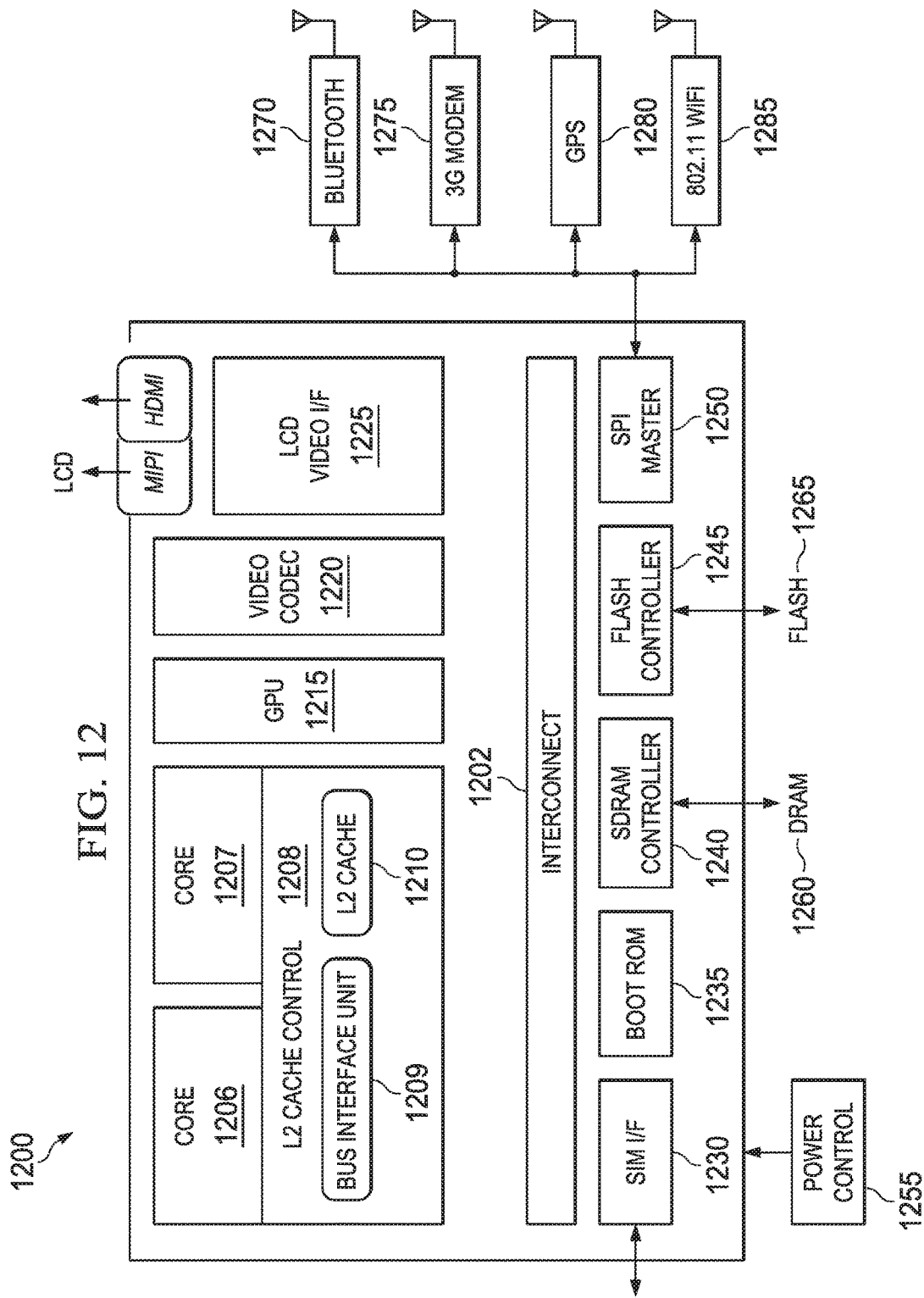
FIG. 12 is a simplified block diagram associated with an example system on chip (SOC) of the present disclosure.

Turning to FIG. 12, FIG. 12 is a simplified block diagram associated with an example ecosystem SOC 1200 of the present disclosure. At least one example implementation of the present disclosure can include the keycap with active elements features discussed herein. For example, the architecture can be part of any type of tablet, smartphone (inclusive of Android™ phones, iPhones™), iPad™, Google Nexus™, Microsoft Surface™, personal computer, server, video processing components, laptop computer (inclusive of any type of notebook), Ultrabook™ system, any type of touch-enabled input device, etc.

In this example of FIG. 12, SOC 1200 may include multiple cores 1206-1207, an L2 cache control 1208, a bus interface unit 1209, an L2 cache 1210, a graphics processing unit (GPU) 1215, an interconnect 1202, a video codec 1220, and a liquid crystal display (LCD) I/F 1225, which may be associated with mobile industry processor interface (MIPI)/high-definition multimedia interface (HDMI) links that couple to an LCD.

SOC 1200 may also include a subscriber identity module (SIM) I/F 1230, a boot read-only memory (ROM) 1235, a synchronous dynamic random access memory (SDRAM) controller 1240, a flash controller 1245, a serial peripheral interface (SPI) master 1250, a suitable power control 1255, a dynamic RAM (DRAM) 1260, and flash 1265. In addition, one or more example embodiments include one or more communication capabilities, interfaces, and features such as instances of Bluetooth™ 1270, a 3G modem 1275, a global positioning system (GPS) 1280, and an 802.11 Wi-Fi 1285.

In operation, the example of FIG. 12 can offer processing capabilities, along with relatively low power consumption to enable computing of various types (e.g., mobile computing, high-end digital home, servers, wireless infrastructure, etc.). In addition, such an architecture can enable any number of software applications (e.g., Android™, Adobe® Flash® Player, Java Platform Standard Edition (Java SE), JavaFX, Linux, Microsoft Windows Embedded, Symbian and Ubuntu, etc.). In at least one example embodiment, the core processor may implement an out-of-order superscalar pipeline with a coupled low-latency level-2 cache.

Figure 13:
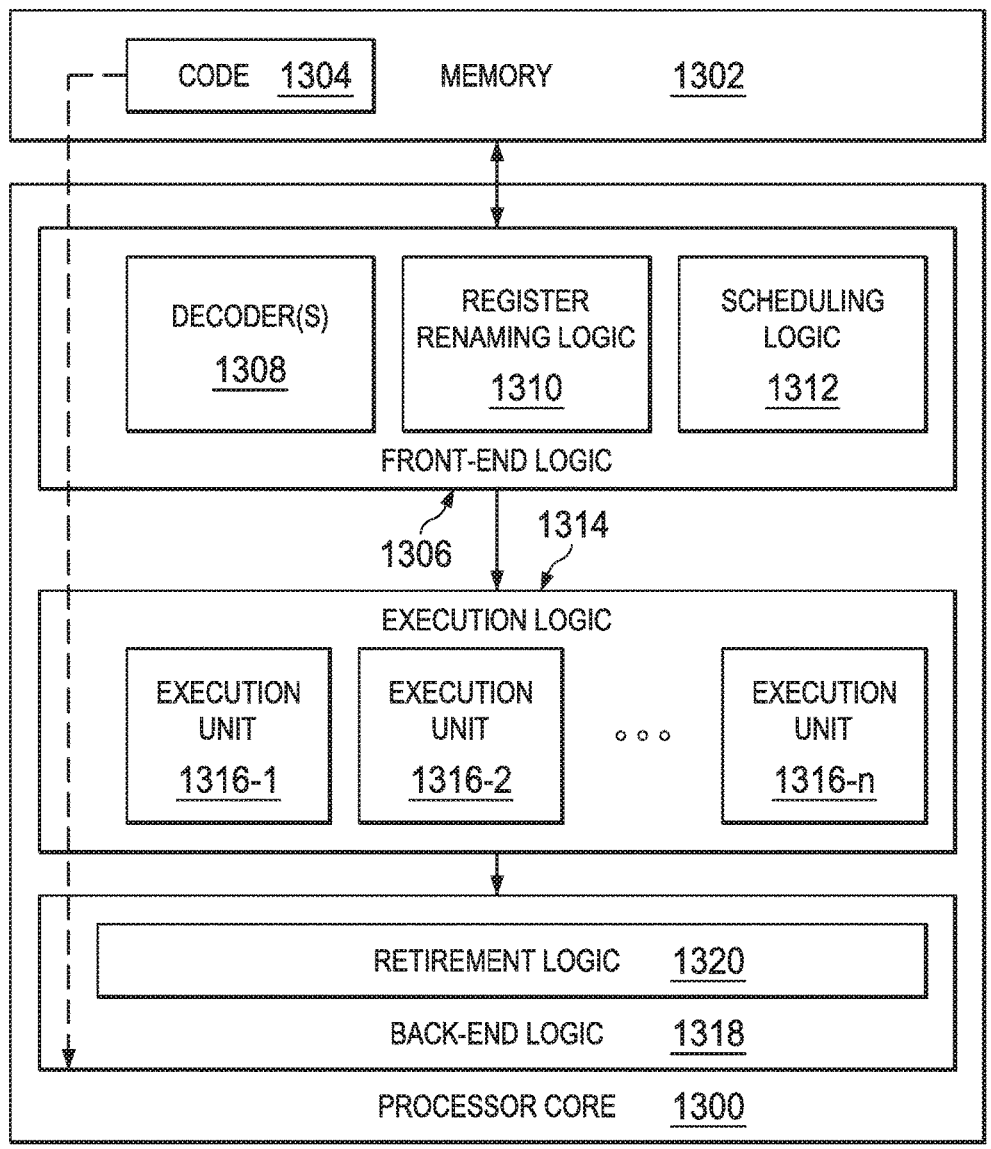
FIG. 13 is a block diagram illustrating an example processor core, in accordance with an embodiment; and The FIGURES of the drawings are not necessarily drawn to scale, as their dimensions can be varied considerably without departing from the scope of the present disclosure.

Turning to FIG. 13, FIG. 13 illustrates a processor core 1300 according to an embodiment. Processor core 1300 may be the core for any type of processor, such as a microprocessor, an embedded processor, a digital signal processor (DSP), a network processor, or other device to execute code. Although only one processor core 1300 is illustrated in FIG. 13, a processor may alternatively include more than one of the processor core 1300 illustrated in FIG. 13. For example, processor core 1300 represents one example embodiment of processors cores 1174a, 1174b, 1174a, and 1174b shown and described with reference to processors 1170 and 1180 of FIG. 11. Processor core 1300 may be a single-threaded core or, for at least one embodiment, processor core 1300 may be multithreaded in that it may include more than one hardware thread context (or "logical processor") per core.

FIG. 13 also illustrates a memory 1302 coupled to processor core 1300 in accordance with an embodiment. Memory 1302 may be any of a wide variety of memories (including various layers of memory hierarchy) as are known or otherwise available to those of skill in the art. Memory 1302 may include code 1304, which may be one or more instructions, to be executed by processor core 1300. Processor core 1300 can follow a program sequence of instructions indicated by code 1304. Each instruction enters a front-end logic 1306 and is processed by one or more decoders 1308. The decoder may generate, as its output, a micro operation such as a fixed width micro operation in a predefined format, or may generate other instructions, microinstructions, or control signals that reflect the original code instruction. Front-end logic 1306 also includes register renaming logic 1310 and scheduling logic 1312, which generally allocate resources and queue the operation corresponding to the instruction for execution.

Processor core 1300 can also include execution logic 1314 having a set of execution units 1316-1 through 1316-N. Some embodiments may include a number of execution units dedicated to specific functions or sets of functions. Other embodiments may include only one execution unit or one execution unit that can perform a particular function. Execution logic 1314 performs the operations specified by code instructions.

After completion of execution of the operations specified by the code instructions, back-end logic 1318 can retire the instructions of code 1304. In one embodiment, processor core 1300 allows out of order execution but requires in order retirement of instructions. Retirement logic 1320 may take a variety of known forms (e.g., re-order buffers or the like). In this manner, processor core 1300 is transformed during execution of code 1304, at least in terms of the output generated by the decoder, hardware registers and tables utilized by register renaming logic 1310, and any registers (not shown) modified by execution logic 1314.

Although not illustrated in FIG. 13, a processor may include other elements on a chip with processor core 1300, at least some of which were shown and described herein with reference to FIG. 11. For example, as shown in FIG. 11, a processor may include memory control logic along with processor core 1300. The processor may include I/O control logic and/or may include I/O control logic integrated with memory control logic.

It is imperative to note that all of the specifications, dimensions, and relationships outlined herein (e.g., height, width, length, materials, etc.) have only been offered for purposes of example and teaching only. Each of these data may be varied considerably without departing from the spirit of the present disclosure, or the scope of the appended claims. The specifications apply only to one non-limiting example and, accordingly, they should be construed as such. In the foregoing description, example embodiments have been described. Various modifications and changes may be made to such embodiments without departing from the scope of the appended claims. The description and drawings are, accordingly, to be regarded in an illustrative rather than a restrictive sense.

Although the present disclosure has been described in detail with reference to particular arrangements and configurations, these example configurations and arrangements may be changed significantly without departing from the scope of the present disclosure. Moreover, certain components may be combined, separated, eliminated, or added based on particular needs and implementations. Additionally, although the present disclosure has been illustrated with reference to particular elements and operations that facilitate the communication process, these elements and operations may be replaced by any suitable architecture, protocols, and/or processes that achieve the intended functionality of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

OTHER NOTES AND EXAMPLES

Example A1 is key including a keycap wherein the keycap includes a protective layer and an active element, wherein the height of protective layer and the active element is less than six (6) millimeters in height.

In Example A2, the subject matter of Example A1 can optionally a front plane layer, a back plane layer, where the front plane layer and the back plane layer comprise the active element, and an electrical connection through the keycap to provide electrical communication with the active element.

In Example A3, the subject matter of any one of Examples A1-A2 can optionally include where active element is a display.

In Example A4, the subject matter of any one of Examples A1-A3 can optionally include where the keycap includes a mask layer between about seven (7) microns to about forty-seven (47) micros thick.

In Example A5, the subject matter of any one of Examples A1-A4 can optionally include where wherein the front plane layer may be less than about two-hundred and fifty (250) microns thick.

In Example A6, the subject matter of any one of Examples A1-A5 can optionally include where the backplane layer is less than about two-hundred (200) microns thick.

In Example A7, the subject matter of any one of Example A1-A6 can optionally include where a resin layer, wherein the resin layer is optically clear.

Example M1 is a method including forming a keycap for a key, the keycap including a protective layer and an active element, where the height of protective layer and the active element is less than about six (6) millimeters in height.

In Example M2, the subject matter of Example M1 can optionally include where active element is a display.

In Example M3, the subject matter of any one of the Examples M1-M2 can optionally include where the keycap includes a front plane layer, a back plane layer, where the front plane layer and the back plane layer comprise the active element, and an electrical connection through the keycap to provide electrical communication with the active element.

In Example M4, the subject matter of any one of the Examples M1-M3 can optionally include where the front plane layer is less than about two-hundred and fifty (250) microns thick.

In Example M5, the subject matter of any one of the Examples M1-M4 can optionally include where the backplane layer is less than about two-hundred (200) microns thick.

In Example M6, the subject matter of any one of the Examples M1-M5 can optionally include where the keycap includes a mask layer between about seven (7) microns to about forty-seven (47) micros thick.

In Example M7, the subject matter of any one of the Examples M1-M7 can optionally include where the keycap further includes a resin layer, where the resin layer is optically clear.

In Example M8, the subject matter of any one of the Examples M1-M8 can optionally include where an electrical connection to the active element is established though vias in the keycap In Example AA1, an electronic device can include a first housing, where the first housing includes a keyboard, where the keyboard includes keys and each key includes a keycap, where at least a portion of each keycap includes, a protective layer, a back plane layer, where the front plane layer and the back plane layer comprise the active element, and an electrical connection through the keycap to provide electrical communication with the active element.

In Example, AA2, the subject matter of Example AA1 can optionally include where the active element is a display.

In Example AA3, the subject matter of any one of Examples AA1-AA2 can optionally include where the keycap includes a mask layer between about seven (7) microns to about forty-seven (47) micros thick.

In Example AA4, the subject matter of any one of Examples AA1-AA3 can optionally include where the backplane layer is less than about two-hundred (200) microns thick.

Example X1 is a machine-readable storage medium including machine-readable instructions to implement a method or realize an apparatus as in any one of the Examples A1-A7, or M1-M7. Example Y1 is an apparatus comprising means for performing of any of the Example methods M1-M7. In Example Y2, the subject matter of Example Y1 can optionally include the means for performing the method comprising a processor and a memory. In Example Y3, the subject matter of Example Y2 can optionally include the memory comprising machine-readable instructions.

The invention claimed is:

1. A key comprising:
    a keycap, wherein the keycap includes a pocket, and the pocket includes:
        a protective layer; and
        an active element, wherein a height of protective layer and the active element is less than six (6) millimeters in height.
2. The key of claim 1, wherein active element is a display.
3. The key of claim 1, further comprising:
    a front plane layer;
    a backplane layer, wherein the front plane layer and the backplane layer comprise the active element; and
    an electrical connection through the keycap to provide electrical communication with the active element.
4. The key of claim 3, wherein the front plane layer may be less than about two-hundred and fifty (250) microns thick.
5. The key of claim 3, wherein the backplane layer is less than about two-hundred (200) microns thick.
6. The key of claim 1, wherein the keycap includes a mask layer between about seven (7) microns to about forty-seven (47) micros thick.
7. The key of claim 1, wherein the protective layer is an optically clear resin layer.
8. A method, comprising:
    forming a keycap for a key, the keycap including a pocket, and the pocket includes:
        a protective layer; and
        an active element, wherein a height of protective layer and the active element is less than about six (6) millimeters in height.
9. The method of claim 8, wherein active element is a display.
10. The method of claim 8, wherein the pocket further includes:
    a front plane layer;
    a backplane layer, wherein the front plane layer and the backplane layer comprise the active element; and
    an electrical connection through the keycap to provide electrical communication with the active element.
11. The method of claim 10, wherein the front plane layer is less than about two-hundred and fifty (250) microns thick.
12. The method of claim 10, wherein the backplane layer is less than about two-hundred (200) microns thick.
13. The method of claim 8, wherein the keycap includes a mask layer between about seven (7) microns to about forty-seven (47) micros thick.
14. The method of claim 8, wherein the protective layer is an optically clear resin layer.
15. The method of claim 8, wherein an electrical connection to the active element is established though vias in the keycap.
16. An electronic device, comprising:
    a first housing, wherein the first housing includes a keyboard, wherein the keyboard includes a plurality of keys and at least a portion of the keys includes a keycap, wherein each keycap includes a pocket, and the pocket includes:
        a protective layer; and
        an active element, wherein a height of the protective layer and the active element is less than 6 millimeters in height.
17. The electronic device of claim 16, wherein the active element is a display.
18. The electronic device of claim 16, wherein the pocket further comprising:
    a front plane layer;
    a backplane layer, wherein the front plane layer and the backplane layer comprise the active element; and
    an electrical connection through the keycap to provide electrical communication with the active element.
19. The electronic device of claim 18, wherein the keycap includes a mask layer between about seven (7) microns to about forty-seven (47) microns thick.
20. The electronic device of claim 18, wherein the backplane layer is less than about two-hundred (200) microns thick.

* * * * *

UNITED STATES PATENT AND TRADEMARK OFFICE
CERTIFICATE OF CORRECTION

PATENT NO. : 10,340,101 B2
APPLICATION NO. : 15/749393
DATED : July 2, 2019
INVENTOR(S) : Reji Varghese et al.

Page 1 of 1

It is certified that error appears in the above-identified patent and that said Letters Patent is hereby corrected as shown below:

In the Claims

In Column 13, Line 44, in Claim 6, delete "micros;" and insert -- microns; --, therefor.

In Column 14, Line 18, in Claim 13, delete "micros;" and insert -- microns; --, therefor.

In Column 14, Line 22, in Claim 15, delete "though;" and insert -- through; --, therefor.

In Column 14, Line 45, in Claim 19, delete "micros;" and insert -- microns; --, therefor.

Signed and Sealed this
Tenth Day of September, 2019

Andrei Iancu
*Director of the United States Patent and Trademark Office*